(12) United States Patent
Wicks et al.

(10) Patent No.: US 11,091,754 B2
(45) Date of Patent: *Aug. 17, 2021

(54) POROUS MATRICES FOR CULTURE AND FORMULATION OF AGRICULTURAL BIOPESTICIDES AND CHEMICALS

(71) Applicant: LiveGrow Bio LLC, Pasco, WA (US)

(72) Inventors: Alan Stuart Wicks, Kennewick, WA (US); Grigoriy E. Pinchuk, Richland, WA (US)

(73) Assignee: LiveGrow Bio LLC, Pasco, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/675,099

(22) Filed: Nov. 5, 2019

(65) Prior Publication Data
US 2020/0305438 A1 Oct. 1, 2020

Related U.S. Application Data

(63) Continuation of application No. 14/624,257, filed on Feb. 17, 2015, now Pat. No. 10,517,302.

(60) Provisional application No. 61/940,795, filed on Feb. 17, 2014.

(51) Int. Cl.
| C12N 11/02 | (2006.01) |
| A01N 63/38 | (2020.01) |
| A01N 63/22 | (2020.01) |
| A01N 63/27 | (2020.01) |
| C12N 11/14 | (2006.01) |

(52) U.S. Cl.
CPC .............. *C12N 11/02* (2013.01); *A01N 63/22* (2020.01); *A01N 63/27* (2020.01); *A01N 63/38* (2020.01); *C12N 11/14* (2013.01)

(58) Field of Classification Search
None
See application file for complete search history.

(56) References Cited

U.S. PATENT DOCUMENTS

| 4,149,937 A | 4/1979 | Messing et al. |
| 4,153,510 A | 5/1979 | Messing et al. |
| 5,068,105 A | 11/1991 | Lewis et al. |
| 6,080,329 A | 6/2000 | Dobry |
| 6,250,846 B1 * | 6/2001 | Kawabata ............. E02D 3/11 405/128.45 |
| 6,599,503 B2 | 7/2003 | da Luz |
| 7,422,737 B1 | 9/2008 | Nussinovitch et al. |
| 7,854,926 B2 | 12/2010 | Spittle |
| 2003/0152554 A1 | 8/2003 | Gunner et al. |
| 2006/0243011 A1 | 11/2006 | Someus |
| 2008/0064598 A1 | 3/2008 | De Rougemont et al. |
| 2009/0163598 A1 | 6/2009 | Truong |
| 2010/0035347 A1 | 2/2010 | Defez |
| 2011/0229930 A1 | 9/2011 | Menashe |
| 2012/0276054 A1 | 11/2012 | Williams et al. |

FOREIGN PATENT DOCUMENTS

WO 00/62826 A1 10/2000

OTHER PUBLICATIONS

Ashwini et al., "Potentiality of *Bacillus subtilis* as biocontrol agent for management of anthracnose disease of chilli caused by *Colletotrichum gloesorporioides* OGC1," *3 Biotech* 4:127-136, 2014.
Boodley et al., "Cornell Peat-Lite Mixes for Commercial Plant Growing," Information Bulletin 43, Cooperative Extension Publication, Cornell University, N.Y., 1982.
Buée et al., "The rhizosphere zoo: An overview of plant-associated communities of microorganisms, including phages, bacteria, archaea, and fungi, and some of their structuring factors," *Plant Soil* 321:189-212, 2009.
Compant et al., "Use of Plant Growth-Promoting Bacteria for Biocontrol of Plant Diseases: Principles, Mechanisms of Action, and Future Prospects," *Applied and Environmental Microbiology* 71(9):4951-4959, 2005.
De La Fuente et al., "phlD-based genetic diversity and detection of genotypes of 2,4-diacetylphloroglucinol-producing *Pseudomonas fluorescens*," *FEMS Microbiology Ecology* 56(1):64-78, 2006.
Extended European Search Report dated Sep. 29, 2017, issued in corresponding European application No. EP 15 74 8858, filed Feb. 17, 2015, 6 pages.
Gordeeva et al., "Formation of Porous Vermiculite Structure in the Course of Swelling," *Russian Journal of Applied Chemistry* 75(3):357-361, 2002.
Graham-Weiss et al., "Production of Bacterial Inoculants by Direct Fermentation on Nutrient-Supplemented Vermiculite," *Applied and Environmental Microbiology* 53(9):2138-2140, 1987.
Hölker et al., "Biotechnological advantages of laboratory-scale solid-state fermentation with fungi," *Applied Microbiology and Biotechnology* 64:175-186, 2004.
Hongzhang et al., "Alkaline Protease Production by Solid State Fermentation on Polyurethane Foam," *Chemical and Biochemical Engineering Quarterly* 20(1):93-97, 2006.
Idris et al., "Use of *Bacillus subtilis* as biocontrol agent. VI. Phytohormone-like action of culture filtrates prepared from plant growth-promoting *Bacillus amyloliquefaciens* FZB24, FZB42, FZB45 and *Bacillus subtilis* FZB37," *Journal of Plant Diseases and Protection* 111(6):583-597, 2004.
International Preliminary Examination Report dated Sep. 1, 2016, issued in corresponding International Application No. PCT/US2015/016210, filed Feb. 17, 2015, 7 pages.
International Search Report and Written Opinion dated Jun. 4, 2015, issued in corresponding International Application No. PCT/US2015/016210, 7 pages.

(Continued)

*Primary Examiner* — Katherine Peebles
(74) *Attorney, Agent, or Firm* — Seed Intellectual Property Law Group LLP

(57) ABSTRACT

The present disclosure addresses biologically active formulations for agricultural and other applications that comprise a solid growth substrate that defines an open cell matrix and an active population of one or more microorganisms adhered thereto. The formulation is configured to be applied directly to a plant growth environment and does not require additional isolation and/or processing steps that would separate the microorganisms from the solid growth substrate prior to deployment. The disclosure also addresses related methods.

20 Claims, No Drawings

(56) References Cited

OTHER PUBLICATIONS

Joseph et al., "Enrichment of Feed Ingredients Through Solid State Fermentation," Technical Paper 18, in "Winter School on Recent Advances in Mariculture Genetics and Biotechnology," Course Manual, Indian Council of Agricultural Research, Central Marine Fisheries Research Institute, Tatpuram, Kochi, India, Nov. 4-24, 2003, 6 pages.

Lemon et al., "Biofilm Development with an Emphasis on *Bacillus subtilis*," *Current Topics in Microbiology and Immunology* 322:1-16, 2008.

Matroudi et al., "Antagonistic effects of three species of *Trichoderma* sp. on Sclerotinia sclerotiorum, the causal agent of canola stem rot," *Egyptian Journal of Biology* 11:37-44, 2009.

McQuilken et al., "Application of Microorganism to Seeds," in H.D. Burges (ed.), *Formulation of Microbial Biopesticides: Beneficial Organisms, Nematodes and Seed Treatments*, Kluwer Academic Publishers, Dordrecht, Netherlands, Chap. 8, pp. 255-285, 1998.

Raimbault, "General and microbiological aspects of solid substrate fermentation," *Electronic Journal of Biotechnology* 1(3):1-15, 1998.

Ralebitso et al., "Microbial Aspects of Atrazine Degradation in Natural Environments," *Biodegradation* 13(1):11-19, 2002.

Talboys et al., "Auxin secretion by *Bacillus amyloiquefaciens* FZB42 both stimulates root exudation and limits phosphorus uptake in *Triticum aestivum*," *BMC Plant Biology* 14(51):1-9, 2014.

Tian et al., "Bacteria used in the biological control of plant-parasitic nematodes: populations, mechanisms of action, and future prospects," *FEMS Microbiology Ecology* 61:197-213, 2007.

Arsenović et al., "Serbian heavy clays behavior: Application in rouch ceramics," *Hem. Ind.* 67(5):811-822, 2013.

Fátima Júlio et al., "Aerogel-based renders with lightweight aggregates: Correlation between molecular/pore structure and performance," *Construction and Building Materials* 124:485-495, 2016.

Krupskaya et al., "Experimental Study of Montmorillonite Structure and Transformation of Its Properties under Treatment with Inorganic Acid Solutions," *Minerals* 7(49), 2017. (15 pages).

Samar et al., "Study of Chemical and Physical Properties of Perlite and Its Application in India," *International Journal of Science Technology and Management* 5(4):70-80, 2016.

Tsai et al., "Characterization and adsorption properties of diatomaceous earth modified by hydrofluoric acid etching," *Journal of Colloid and Interface Science* 297:749-754, 2006.

\* cited by examiner

POROUS MATRICES FOR CULTURE AND FORMULATION OF AGRICULTURAL BIOPESTICIDES AND CHEMICALS

CROSS-REFERENCE TO RELATED APPLICATION

This application claims the benefit of U.S. Provisional Patent Application No. 61/940,795, filed Feb. 17, 2014, which is incorporated herein by reference in its entirety.

BACKGROUND

Growing populations and economies have resulted in a steady need to increase agricultural output. Chemical pesticides and synthetic plant growth regulators have been applied as part of a greater effort to increase the efficiency of agricultural production. However, such agricultural additives are recognized as often having serious environmental and public health issues. Additionally, continuous and/or over-application of many pesticides have led to tolerance in many plant and animal pathogens. Accordingly, there are efforts to replace the application of synthetic chemicals with the use of more environmentally friendly approaches. Such approaches include use of living microorganisms and the biochemicals produced by naturally occurring microorganisms as agricultural formulations to control pests or provide natural plant growth regulators.

However, current methods of growing and formulating living microorganisms for agricultural applications rarely generate products that are cost effective, especially for low value crops. Current approaches for generating the living bioproducts, and applying them to the target crops, have generally resulted in large production inefficiencies, reduced efficacies of the produced microorganisms and reduced microbial survival/colonization in treated environments. Current formulations of microorganisms have failed to meet optimal performance expectations primarily because the organisms are typically cultured under conditions that are very divergent from their normal environment and the environment where they are deployed. Furthermore, the organisms undergo extensive post-culture processing to separate them from the growth media and to prepare the microorganisms for storage and distribution. This often results in a bioproduct with a high proportion of the microorganisms existing in a quiescent state, such as a spore form. This creates a slow ramp up time to the point that the microorganisms cannot actively compete against the existing populations in the environment and, therefore, to actively promote or otherwise affect the growth of the plant. Accordingly, these approaches reduce the capacity of the produced microorganisms to successfully colonize the environment to which they are applied. As a result, a significant portion of the applied microorganisms fails to grow or fails to compete with the populations already present in the plant environment.

To compensate for such performance shortfalls of the cultured microorganisms, greater applied quantities of the bioproducts are utilized, requiring a greater investment of initial resources. This typically makes this type of treatment economically uncompetitive or even prohibitive for less lucrative crops.

Accordingly, a need remains for active microorganisms and microbe-based biological products that can be economically produced, distributed, and applied in the field for efficient and effective promotion of plant cultivation. The present disclosure addresses this and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure is directed to a biologically active formulation configured to be applied directly to a plant growth environment comprising a solid substrate that defines an open cell matrix and an active population of one or more microorganisms adhered to the solid substrate.

In another aspect, the disclosure is directed to a method for conditioning a plant growth environment, comprising applying the described agricultural formulation to a plant or a plant growth environment.

In another aspect, the disclosure is directed to a method for conditioning a plant growth environment with an active microorganism culture, comprising:
  inoculating a solid substrate that defines an open cell matrix with one or more active microorganisms under conditions suitable for the establishment of an active microbial population on the solid substrate,
  culturing the one or more active microorganisms on the solid substrate under conditions suitable for the establishment of one or more microorganisms, and
  applying the solid substrate to a plant growth environment.

In another aspect, the disclosure is directed to a method of on-demand production of the described formulation, comprising:
  sterilizing a unit of solid substrate that defines an open cell matrix, wherein the solid substrate optionally contains appropriate growth medium;
  storing the unit of sterilized solid substrate;
  receiving an order for an agricultural formulation;
  inoculating the stored unit of solid substrate with the appropriate one or more microorganisms to create a formulation, as described herein; and
  optionally, ship or transfer the formulation to a user.

DETAILED DESCRIPTION

The present disclosure provides improved bioproduct formulations and related methods for culturing beneficial microorganisms and using the formulations.

Presently, the two general methods of producing microorganisms and products of their metabolism for biological-based agricultural formulations both utilize fermentation processes. One method is referred to as liquid state fermentation (LSF) and the other is referred to as solid state fermentation (SSF).

Liquid state fermentation (LSF) encompasses growing microorganisms in liquid media that is generally gas-sparged and stirred. While LSF is the most commonly used method today for generating products, such as biopesticides, it has serious drawbacks that are well-known in the art. For example, the quality of the biological product is low because the microorganisms tend to be poorly conditioned to the environment to which they will be applied. This is because the culturing environment is highly divergent from the applied environment, potentially permitting an adaptive divergence of the microorganisms away from their natural state. Additionally, the culturing process is expensive for the amount of generated output product because of requirements for expensive equipment, materials, energy, and trained personnel. This culturing approach also incurs a high cost of downstream processing, in particular for extraction of the desired product from the liquid media and preservation for storage and distribution. Furthermore, the environmental costs are high because of large quantities of liquid waste generated during production. The combined impact of such factors restricts the economical application of this technique to mostly high-value agricultural products.

Solid state fermentation (SSF) is generally defined as the fermentation involving solid substrates in the absence or near-absence of free water. However, the substrate must possess sufficient moisture to support growth and metabolism of the microorganisms. There are two general classes of substrates that are used for SSF-based production of bioproducts. The first group includes natural products, which are generally agricultural waste stream products or grains, seeds and pulses. These substrates are readily available to the industry and provide a convenient carbon source for the microorganisms. The second group includes chemically inert solid supports. In contrast to the natural product substrates, chemically inert supports do not provide any food for growth and, thus, require the addition nutrients.

Solid state fermentation systems provide several advantages over the LSF, which are recognized in the literature. For example, SSF provides an increase in both specific quantity and quality of the biological product. For example, the biological products (i.e., microorganisms) produced by SSF are more similar to the corresponding organisms that grow in the natural environment because the growth substrate more closely resembles the natural growth environment in which the microorganisms originally evolved. Similarly, this substrate is likely to be similar to the environment to which the biological products will be applied, thus pre-conditioning the microorganisms to optimally compete with the existing populations in the environment immediately upon application. Furthermore, SSF incurs lower costs related to equipment, materials, energy, and personnel because of the relatively simple technologies involved. SSF also incurs significantly lower costs related to post-culture extraction of the desired product from the solid media because it generally produces more concentrated products, which facilitate downstream processing. Finally, SSF reduces environmental costs because it results in smaller quantities of waste, and more ecologically-friendly waste, as compared to LSF.

While the SSF approach can produce better bioproducts compared to the LSF approach, there are still significant drawbacks with the current SSF formulations that negatively impact their potential efficacy. For example, traditional SSF approaches still result in microorganism populations with reduced survival rates in the field, resulting in formulations that remain suboptimal. Moreover, the desirable biological product is often in a quiescent form of the microorganism, such as a spore. Once extracted and exposed to the environment, these individual microorganisms are more susceptible to death because they are devoid of any shielding against harsh natural conditions and predation. Another SSF disadvantage is that it is generally not suited to produce meaningful amounts of bacterial cells and, thus, is almost exclusively limited to grow fungi. Additionally, the microorganisms often produce useful and desirable biologically-active cell products during the fermentation. However, isolating the active cells and/or spores from the substrate separates the active cells from these desirable cell products, thereby rendering the overall end-product formulation less effective while simultaneously making it more complicated and expensive to produce.

As described in more detail below, the inventors made the surprising discovery that formulations including both 1) the cultured beneficial microorganisms, and 2) the solid substrate upon which the microorganisms are cultured, are effective for various agricultural applications. This approach addresses several problems with the existing practices and technologies and, thus, provides distinct advantages. One advantage is that the production and ultimate formulation effort is simplified. Formulation does not require additional extraction, isolation, or processing steps to remove the cultured microorganism from the solid growth substrate and/or preserve the microorganisms until their eventual deployment. Not only does this simplify the process of making the formulation and reduce the attendant costs, the living microorganisms are also spared from additional processes and conditions that might reduce their viability or alter their desired phenotype. Moreover, a higher proportion of the living microorganisms are likely to remain in their active states, as opposed to reverting to quiescent states (e.g., spore or even in deep-frozen or freeze-dried biomass). Accordingly, upon deployment the microorganisms can immediately begin to influence their environment and compete with the existing populations and, thus, are more likely to establish an active and lasting colony that can immediately and continuously influence their environment, such as promoting positive growing conditions for plants.

Maintaining the association between the solid growth substrate and the cultured microorganisms established thereon also directly promotes the longevity of the microorganism population after deployment or application of the formulation in the environment. A solid growth substrate with an active microorganism population established thereon provides additional protection to the cultured microorganisms during and after application to the field. Thus, the applied formulation of the present disclosure can maintain a protective barrier against invasion by competing microorganisms present in the target environment. Because the culture is well-established in the solid substrate upon application to the target environment, the formulation acts as a micro-environment that is difficult for competing microorganisms to colonize. Thus, after deployment in the field, the formulation can serve as a shelter that continuously produces and exports beneficial microorganisms (and/or their products), with lowered risk of depletion of the source colonies established within the solid support. Combined, these advantages provide for an economical, high-quality, and long-lasting effect of the deployed formulation. As a result, an effective use or treatment requires a lower quantity of applied microorganisms, further reducing the attendant economic and environmental costs of production and deployment.

In accordance with the foregoing, in one aspect the present disclosure provides a biologically active formulation comprising a solid substrate and an active population of one or more microorganisms adhered to the solid substrate.

In one embodiment, the formulation is configured to be applied directly to a plant growth environment. In this regard, the formulation does not require any additional processing to remove or isolate the active population of one or more microorganisms from the solid substrate. In contrast, the solid substrate in association with the active population of one or more microorganisms adhered thereto can be applied directly to the plant growth environment. Accordingly, it is preferred that the solid substrate is appropriate for the particular plant growth environment and is conducive to, or at least not detrimental to, the growth conditions of the intended plant in the environment. The plant growth environment can be any environment in which a plant of interest is cultivated, such as in soil or a soil mix disposed in a field, greenhouse or shade house, in an aquaculture preparation, an in vitro medium, and the like.

Accordingly, in some embodiments, the formulation is an agricultural formulation. As used herein, the term "agricultural" refers to the growth and/or cultivation of any plant of interest. Thus, the term implies the potential application of the formulation to the cultivation of plant products for food or fuel production, for horticultural or ornamental interests, for sports and recreation, and the like. Non-limiting examples of plants for food or fuel production are well-known and include commodity crops such as corn, wheat, sorghum, soybeans, citrus and non-citrus fruits, nut trees, and the like. Non-limiting examples of plant horticultural or ornamental interests are also well-known. Finally, non-limiting examples of plants for sports and recreations include turf grasses for sports fields and golf courses. As an agricultural formulation that is figured to be applied directly to a plant growth environment, the present formulation can be in any form that can be conveniently applied to the plant growth environment without extensive processing. For example, the formulation of the present aspect may be shredded or in pellet form that can be spread over a field or mixed with a soil. In another example, the formulation may be in a solid sheet that can be spread over a soil surface. In a further example, the sheet may be later churned into the soil, thereby fragmenting the sheet into small particles or pieces.

The solid substrate can comprise any known solid material that is known to provide a solid support structure to permit and/or promote the growth of microorganisms. In one embodiment, the solid material is inert and, thus, does not itself provide any direct nutrients for the microorganisms. In such an embodiment, the formulation can be supplemented with the appropriate growth medium to provide nutrients supporting the growth and maintenance of the microorganisms. In another embodiment, the solid material is organic. In further embodiments, the solid material can also serve as a nutrient source for the microorganisms. However, the solid material will preferably maintain sufficient structural integrity over time (e.g., days and/or months) to provide a lasting solid support for the one or more microorganisms. Illustrative, non-limiting solid materials that are useful for the present formulation include cellulose, lignocellulose, pectin, starch, perlite, vermiculite, zeolite, ceramic, metal, glass, and any other material known to provide solid support for the culture of microorganisms.

To promote a robust population of the one or more microorganisms, the solid substrate can define a solid matrix with a high surface to volume ratio. Such a configuration provides ample surface area for attachment of a high number of individual microorganisms in the population. Additionally, the organization of the matrix mimics the physical structure of the natural growth environment of many beneficial microorganisms, such as the physical matrix provided by sand and soil. In one embodiment, the solid substrate defines an open cell matrix. As used herein, the term "open cell matrix" refers to a configuration of the solid support that has a plurality of open cells (also referred to as "pores") and/or channels. The term "open" refers to the fluid or gaseous communication between the cells and the outside environment of the solid substrate. The cells can directly open into the outside environment (e.g., with direct fluid communication) and/or be indirectly open to the outside environment (e.g., with indirect fluid communication through other open cells and/or channels.) Thus, the open cell matrix comprises a plurality of open cells, with at least a portion of which being interconnected. Thus, air and/or liquid media can freely circulate throughout the matrix and have access to a plurality of the open cells therein. Under such conditions, the microorganism culture(s) can permeate through the interconnected cells and channels of the matrix because they will maintain access to nutrients, an aerobic environment, and a solid substrate configured for physical attachment and support. Thus, the present formulation will preferably have the microorganisms adhered to the exterior and internal surfaces provided throughout the open cell matrix.

In illustrative embodiments, the matrix comprises a plurality of open cells each having an approximate diameter in the range of about 0.1 µm to about 10 µm, about 0.1 µm to about 100 µm, about 0.1 µm to about 1,000 µm, about 0.1 µm to about 10,000 µm, about 1 µm to about 100 µm, about 1 µm to about 1,000 µm, about 1 µm to about 10,000 µm, about 10 µm to about 100 µm, 10 µm to about 1,000 µm, 10 µm to about 10,000 µm, or any sub-range therein. It will be appreciated that the open cells may not necessarily be spherical or perfectly spherical. Accordingly, as used herein the term "diameter" refers to any relevant measurement of distance from one side to another of the defined open cell that crosses an approximate center position.

The open cell matrix can also be characterized in terms of a ratio between surface area and volume. In illustrative, non-limiting embodiments, the open cell matrix can have a surface area to volume ratio of about $10^3$ $m^2/cm^3$ to about $10^6$ $m^2/cm^3$. However, it will be appreciated that open cell matrices can be used in the present disclosure that fall outside of this range. These are also encompassed by the present disclosure.

In some embodiments, the solid substrate can be one or more independent units, each of which defines an open cell matrix. Each unit, or piece, of solid substrate can be any appropriate size that is amenable to efficient establishment and growth of the intended population microorganism(s). As an illustrative example, as described in more detail below, the present inventors used cellulosic sponges as the solid substrate/open cell matrix for cultivation of a variety of microorganisms, including Gram negative and Gram positive bacteria, as well as fungus. Such solid substrates (e.g., sponges) can be fragmented or in large pieces or sheets, as appropriate.

In some embodiments, the solid substrate comprises a plurality of particles. In one such embodiment, it is the aggregation of the plurality of individual particles in a defined space that defines the open cell matrix. With most shapes, the aggregation of a plurality of particles will result in numerous gaps and spaces where the individual particles do not make mutual contact. Such gaps and spaces can serve as (are equivalent to) the open cells and channels as described above. In another embodiment, the particles themselves are porous and, thus, each defines an open cell matrix as described above. In some embodiments, the plurality of particles comprises particles each with a volume between about 0.03 $mm^3$ and about 1 $cm^3$, 0.03 $mm^3$ and about 5 $cm^3$, 0.03 $mm^3$ and about 10 $cm^3$, 0.03 $mm^3$ and about 100 $cm^3$, about 0.1 $mm^3$ and about 1 $cm^3$, 0.1 $mm^3$ and about 5 $cm^3$, 0.1 $mm^3$ and about 10 $cm^3$, 0.1 $mm^3$ and about 100 $cm^3$, 0.1 $mm^3$ and about 5 $cm^3$, 1 $mm^3$ and about 10 $cm^3$, 1 $mm^3$ and about 100 $cm^3$, or any sub-range therein.

As indicated above, the formulation can be characterized as biologically active. This quality results from the component of a live, active culture of one or more microorganisms adhered to the solid substrate. The biological activity that is pertinent to the quality and/or performance of the formulation refers to the activity of the living microorganisms. This biological activity can be, for instance, for the intended purpose of affecting a plant and/or its growth environment. It will be appreciated that the affect can be positive or negative, depending on the ultimate intent or design of the application. For instance, it may be desired to provide a formulation with microorganisms that negatively affect the growth of a particular weed. In other embodiments, it may be desired to provide a formulation with microorganisms that positively affect the growth conditions of a particular plant by producing a nutrient or by negatively affecting the conditions for plant pathogens within the plant growth environment.

Thus, in some embodiments the microorganisms can be producers of any desired product that is useful for an intended purpose, such as affecting the environment of a plant. Such a product can be any known biologically active compound capable of being produced by a microorganism. Illustrative, non-limiting products include pesticides, herbicides, plant nutrients, biostimulants, metal chelators, beneficial enzymes, antibiotics, and the like. See, e.g., (Compant, S., et al., "Use of Plant Growth-Promoting Bacteria for Biocontrol of Plant Diseases: Principles, Mechanisms of Action, and Future Prospects—A Mini-Review," *Appl. Environ. Microbiol.* 71(9):4951-4959 (2005); Tian, B., et al., "Bacteria used in the biological control of plant-parasitic nematodes: populations, mechanisms of action, and future prospects—A Mini-Review," *FEMS Microbiol Ecol* 61:197-213 (2007); T. Butt, et al. (eds), "Fungi as Biocontrol Agents—Progress, Problems and Potential." Oxen, England: CABI, 2001 Print., each incorporated herein by reference in its entirety). Such products can be produced from endogenous genes of the microorganism or from heterologous genes recombinantly introduced into the microorganisms. Recombinant microorganisms for the production of desired products can be generated according to any well-established techniques in the art. Illustrative products currently commercially available are based on the fungi *Beauveria bassiana* (e.g., Mycotrol®, Cease™, BotaniGard®) and *Trichoderma* species (e.g., T-22, Biocon, Bioguard®, Ecofit, F-Stop, Soilguard®). Additional bacterial product that contain *Bacillus thuringiensis* are also known.

In other embodiments, the one or more microorganisms adhered to the solid substrate may serve as predators of other, undesired microorganisms. Examples of such predators are the predaceous fungi. These are fungi that derive some or most of their nutrients from trapping and eating microscopic or other minute animals. More than 200 species have been described belonging to the phyla Ascomycota, Mucoromycotina, and Basidiomycota. They usually live in soil and many species trap or stun nematodes (nematophagous fungus), while others attack amoebae or collembola. Examples of nematophagous fungi are *Dactylaria* sp., *Monacrosporium* sp., and *Arthrobotrys* sp.

In yet other embodiments, the one or more microorganisms may consume certain pollutants that may be toxic or inhibitory to a desired plant. The herbicide atrazine has been a focus of interest for some time (Ralebits, T. K., et al., "Microbial aspects of atrazine degradation in natural environments," *Biodegradation* 13(1):11-9 (2002), incorporated herein by reference in its entirety). Such microorganisms could serve in a formulation designed for soil remediation, such as after contamination or application of toxins.

In another embodiment, the biological activity provided by the microorganisms is merely to provide competition for common resources utilized by undesired microorganisms present in the plant growth environment.

As indicated above, the formulation comprises an active population of one or more microorganisms. Unless stated otherwise, the phrase "population of one or more microorganisms" refers to a population of one or more microorganism types, such as species or species strains of a microorganism. Thus, the formulation can have one, two, three or more different types of microorganisms established on and within the solid substrate. The term "population" refers to all individuals in the aggregate of microorganisms and indicates that there are multiple individuals of each of the one or more microorganism types. The term "portion" of a population refers to all, or less than all, individuals of the aggregate of all microorganism, but does not necessarily imply a division between individuals of different type.

The one or more microorganisms can include microorganisms that are prokaryotic and/or eukaryotic.

Prokaryotic microorganisms include archaebacteria, Gram-negative eubacteria, Gram-positive eubacteria, and cyanobacteria.

Illustrative, non-limiting examples of archaebacteria that are useful in the present disclosure include archaebacteria found in plant rhizosphere and are suggested to play an important role in elemental cycling (see, e.g., Bue M., et al., "The Rhizosphere Zoo: An Overview of Plant-Associated Communities of Microorganisms, Including Phages, Bacteria, Archaea, and Fungi, and Some of Their Structuring Factors," *Plant Soil* 321:189-212 (2009), incorporated herein by reference in its entirety). The role of archaebacteria interaction with plants is currently under extensive research and future results may put forward additional prospective candidates for new biological products.

Illustrative, non-limiting examples of Gram-negative eubacteria that are useful in the present disclosure include bacteria belonging to *Pseudomonas, Lysobacter, Rhizobium, Serratia, Methylobacterium, Agrobacterium, Azospirillum*, and *Azotobacter*. It is noted that, heretofore, formulation of these bacteria has been the main technological problem for applying Gram-negative bacteria for biological applications. While spore forming microbes such as *Bacillus* and fungi are relatively easy to formulate into dry preparations, Gram-negative bacteria do not have known resting forms that allow survival of big part of population upon dehydration. As the result, these microbes have to be frozen or freeze-dried for deferred use. Both approaches drive a large-scale die off of the population while making the final products too expensive for most applications in agriculture and other areas. Thus, improvement of Gram-negative bacteria survival upon prolonged storage has become an important research target (see, e.g., Burges, H. D. [ed.]"Formulation of Microbial Biopesticides: Beneficial Organisms, Nematodes and Seed Treatments," Dordrecht, The Netherlands: Kluwer Academic Publishers, 1998 (pp. 255-285), incorporated herein by reference in its entirety.) The present disclosure overcomes this problem because the bacteria do not require a quiescent state for long term storage or any additional processing to remove them from an active culture state.

Illustrative, non-limiting examples of Gram-positive eubacteria that are useful in the present disclosure include bacteria belonging to *Bacillus, Paenibacillus, Streptomyces*, and *Arthrobacter*. In particular, several *Bacillus* and *Streptomyces* species has been used to manufacture biological pesticides (see for example such products on the market as Actinovate WP®, Cease®, Sonata®).

Illustrative, non-limiting examples of cyanobacteria that are useful in the present disclosure include cyanobacteria belonging to *Anabaena, Nostoc* and Nodularia. Some cyanobacteria have been used to spray over fields for nitrogen fixation and producing nitrate, whereas at least one species has shown nematicidal features.

Eukaryotic microorganisms include fungi and protozoa.

Illustrative, non-limiting examples of fungi that are useful in the present disclosure include *Absidia* sp., *Altemaria* sp., *Alternaria* sp., *Amylomyces* sp, *Arthrobotrys* sp., *Aspergillus* sp., *Aureobasidium, Beauveria* sp., *Bipolaris* sp., *Cladosporium* sp., *Dactylaria* sp., *Fusarium* sp., *Geotrichum* sp., *Lentinus* sp., *Metharizium* sp., *Monacrosporium* sp., *Monilia* sp., *Mucor* sp., *Nigrospora, Paecilomyces, Penicilium* sp., *Phanerochaete* sp., *Pleurotus* sp., *Rhizopus* sp., *Rhizopus* sp., *Scopulariopsis* sp., and *Trichoderma* sp.

Illustrative, non-limiting examples of protozoa that are useful in the present disclosure include giant protozoa of the Vampyrellidae (*Arachnula, Thecamoeba, Saccamoeba, Vampyrella*). These protozoa are able to perforate vegetative spores (conidia) of a fungus (*Cochliobolus sativus*), which causes root rot on barley (*Hordeum vulgare* L.; Old, 1967). Without control, root rot reduces winter survival of barley by 20%-60%.

As indicated, the formulation can include one or more microorganism types. It will be appreciated that any compatible combination of any of the microorganisms indicated above can be used in the formulation. A person of skill in the art will readily appreciate which combinations are compatible, or can readily assess compatibility of a combination by applying standard culturing techniques and assessing the establishment of each microorganism type in the co-culture.

As used herein, the phrase "active population" indicates that the population of microorganisms comprises a portion that is not quiescent. The portion need not be restricted to one microorganism type unless there is only one type of microorganism in the population. The state of quiescence can refer to a state of dormancy or inactivity, and can include stages where the microorganism forms a spore. In such a state, the microorganism slows or suspends much of its biological activity. Thus, an active population indicates that at least a portion is not quiescent, but rather is in an active phase demonstrating biological activity, such as metabolic activity, protein production, cell division, and the like. This aspect is associated with several potential benefits conferred by the described formulation because an active population of microorganisms will be able to immediately affect the environment upon deployment without any delay associated with exiting in a quiescent stage. This can allow for enhanced competitiveness against the microbial populations already present in the environment and/or immediate delivery of a biological product to affect the plant growth environment.

In some embodiments, the active population can be characterized as a "defined culture" of one or more microorganisms. As used herein, the term "defined culture" indicates that the population includes known and intended microorganism types and is substantially void of any contaminating microorganism types. Thus, in some embodiments, the defined culture consists essentially of known and intended microorganisms. This quality can distinguish the active population from a general population of microorganisms growing in a solid substrate in the general environment.

In one embodiment, the population of one or more microorganisms, or a portion thereof, is associated with a biofilm on an internal surface of the solid substrate. Some microorganisms, such as *Pseudomonas aeruginosa* or *Bacillus subtilis*, can form a biofilm. In fact, the ability to form biofilms under certain conditions is almost universal among bacteria (see, e.g., Lemon, K. P., et al., "Biofilm Development With an Emphasis on *Bacillus subtilis*," *Curr. Top. Microbiol. Immunol.* 322:1-16 (2008), incorporated herein by reference in its entirety). A biofilm is generally defined as an aggregation of microorganisms in which the cells are embedded within a self-produced extracellular matrix of polymers, such as nucleic acids, proteins, and polysaccharides. The extracellular matrix assists the microorganisms to establish an attachment or adherence to each other and/or to a surface. In certain embodiments, the presence of a biofilm in the formulation assists the stability of the population of one or more microorganisms, or a portion thereof, within the formulation. This can contribute to a longer life-span of the biologically active formulation before or after deployment. However, it will be readily appreciated by persons of skill in the art that a biofilm is not crucial to the utility of the present disclosure. Thus, in some embodiments, the formulation does not include a biofilm.

As indicated above, one advantage of the present formulation is that there is no requirement to further isolate and/or process the population of one or more microorganisms from the solid substrate. Instead, the culture of one or more microorganisms as established within the solid substrate is used as the formulation, which combines both the microorganism and the solid growing substrate, and which is deployed as an end product for a particular purpose such as promoting growing conditions of a plant or remediating soil. Accordingly, in another aspect, the present disclosure provides a method for conditioning a plant growth environment. The method comprises applying any formulation as described herein to a plant or plant growth environment.

As used herein, the term "plant growth environment" refers to any environment that affects the growth of a plant. This is typically an environment in which the plant will be directly cultivated. Non-limiting examples include soil, soil mixes, hydroponic medium or other in vitro cultivation media, and the like. As used herein, the term "soil mixes" refers to any solid medium that incorporates soil as one component. Soil mixes are often designed for the cultivation of various plant varieties that have different requirements or optimal conditions for development. For example, soil mixes can include mixtures of soil, sand, peat, and/or compost, in various ratios. The particular mixes can be designed for parameters such as organic content, mineral content, porosity, water retention, and the like. See, e.g., Boodley, J. W. and R. Sheldrake, Jr., "Cornell Peat-Lite Mixes for Commercial Plant Growing," Information Bulletin 43, A Cornell Cooperative Extension Publication, Cornell University, N.Y. 1982, incorporated herein by reference in its entirety.

In some embodiments, the formulation can be applied directly to any portion of the plant, such as a seed, vegetative cuttings, root, rhizome, bulbs, tuber, stem, flower, fruit, and/or leaf of the plant. For example, the formulation described herein can be mixed with batches of seeds prior to planting in the field. As another example, roots or bulbs can be wrapped in fragments of the formulation prior to planting in soil or soil mixes.

In yet another aspect, the present disclosure provides a method for conditioning a plant growth environment with an active microorganism culture. The method comprises inoculating a solid substrate as described herein with one or more active microorganisms under conditions suitable for the establishment of an active microbial population on the solid substrate, culturing the one or more active microorganisms on the solid substrate under conditions suitable for the establishment of one or more microorganisms, and applying the solid substrate to a plant growth environment.

As described above, the microorganisms encompassed by the present disclosure are well-known for their beneficial properties as part of biological treatments of soil and plant cultivation. Accordingly, the appropriate conditions for inoculation to establish and maintain an active culture of one (or a combination of more than one) of the appropriate microorganisms are well-known, are commonly practiced, and described elsewhere.

As described above, an advantage to the described formulation and uses thereof is that it avoids steps of isolation or further processing. This not only simplifies the entire process from initial culturing and production through deployment, but also provides for a more robust biological activity obtained from the cultures and, thus, requires a significantly less amount of starting material. Accordingly, in preferred embodiments, the microorganisms are not isolated from the open cell matrix.

The plant growth environments of this aspect are described above. In some embodiments, the step of applying the solid substrate directly to the surface of a plant is described as above.

In some embodiments, the solid substrate is applied to the plant growth environment within, on, or about 90 days of inoculating the solid substrate, such as within about 1, 3, 5, 7, 10, 15, 20, 25, 30, 35, 40, 45, 50, 55, 60, 65, 70, 75, 80, 85, and 90 days, or any range or number therein. This is in contrast to present practices, where a cultured microorganism is isolated from its growth medium, processed for storage, stored for prolonged periods, and transported upon the eventual demand for application. Such processing and storage results in a loss of activity, whether due to quiescence, loss of viability, or change in phenotype of the microorganism.

In another aspect the present disclosure provides a convenient method or system to flexibly produce formulations of active microbial cultures, as described herein, on demand. To achieve this, separate units of solid substrate impregnated with appropriate growth medium are prepared through the year, tightly sealed to avoid water evaporation and drying, sterilized by autoclaving or using other methods known in the art, and stored until needed. When biological product order for a specific timeframe is obtained, the necessary amount of these units is inoculated by one or more microorganisms, incubated under appropriate temperature, and shipped after an appropriate growth period. In some embodiments, the microbial growth can occur while units are in the transit to the user, thus obviating the need for any prolonged incubation period prior to shipping of the units. Units can be containers such as plastic bags, plastic, metal, glass cans or any other appropriate containment known in the art, capable of holding an amount of the solid substrate and growth medium in a sterile state for a prolonged period. If targeted microorganisms are aerobic, the units can have appropriate connection to the air provided through membranous shields against contamination. The volume of a unit can vary widely depend on the way they would be used. This aspect allows the provision of live, active microbial cultures to customers/users in a responsive manner. The production of formulation is performed on demand and, thus, can be performed at any time a request is made and in amounts requested, thus avoiding overproduction and a corresponding consumption of resources. Additionally, this approach avoids the production inefficiencies that have traditionally stemmed from seasonal spikes and voids of demand through a yearly cycle of production. Furthermore, this approach avoids a requirement for processing and long-term storage of the formulation, which as described above, reduces the efficacy of the live cultures.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Words such as "about" and "approximately" imply minor variation around the stated value, usually within a standard margin of error, such as within 10% or 5% of the stated value.

Disclosed are materials, compositions, and components that can be used for, in conjunction with, in preparation for, or are products of the disclosed methods and compositions. It is understood that when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are provided to illustrate exemplary approaches for practicing aspects of the present disclosure and are not intended to limit the scope of the disclosure.

Example 1

This example describes a study demonstrating the efficacy of a formulation combining different open-cell solid substrates and the active microbial culture of an additional Gram negative bacteria, *Pseudomonas fluorescens*, established thereon to inhibit the growth of a fungal plant pathogen.

Methods and Materials

Solid Substrate Preparation for Growth Experiments

100% cellulosic household sponges (Industrial Commercial Supply Co, Akron, Ohio) were used to grow bacteria and fungi (pieces of sponge in the range of 2-5 mm and irregularly shaped were generally employed). The sponges were first washed under running tap water for 20 minutes to remove chemical preservatives added by the manufacturer to prevent microbial growth following with distilled water wash and drying for several days at room temperature.

Viscopearl® A model AH-2050L (Rengo Co., LTD, Japan) (also referred to herein as "Viscopearl") cellulose beads were also tested as a potential porous substrate for bacterial growth.

The sponge and Viscopearl® beads were sterilized by autoclaving prior to any inoculation with bacterial cultures. Specifically, sponge or Viscopearl was weighed in portions and placed in glass tubes covered with aluminum foil. The tubes were autoclaved for 30 minutes at 121° C. and, after cooling, the material was used in the same glass tubes or aseptically transferred into sterile 50 ml plastic tubes until further use.

Solid Substrate Absorption Capacity

To estimate sponge water absorption capacity, a sponge piece of known weight was impregnated with distilled water in a container placed on a scale. Water was added gradually until it started to flow out of the sponge. The ratio of water absorbed by sponge to initial weight of dry sponge was defined as water absorption capacity (WAC). For sponges used, WAC was determined to be between 14 and 18.

A similar approach was used to test the water absorption capacity of the Viscopearl® A model AH-2050L cellulose beads. The WAC of the beads was estimated to be 5.

Bacterial Growth in Cellulosic Substrates

*Pseudomonas fluorescens* strain Pf-5 (also referred to herein as "Pf-5") was obtained from USDA-NRRL and grown on King Medium B (KMB) agar plates for 2-3 days. A sterile flask (100 mL capacity) with 15 ml of liquid ⅓ KMB was inoculated from the plate and incubated static with occasional shaking at 23° C.±1° C. for 24-40 hours. The culture was diluted to $10^6$ CFU/ml based on absorbance at 600 nm measured using a Lambda 3A UVNIS Spectrophotometer (Perkin Elmer) and plastic cuvettes with 1 cm light path length ($OD_{600}$ at 0.1 corresponds to $0.5 \times 10^8$ CFU/ml); see, e.g., De La Fuente, L., et al., "phlD-Based Genetic Diversity and Detection of Genotypes of 2,4-Diacetylphloroglucinol-Producing *Pseudomonas fluorescens*," *FEMS Microbiol. Ecol.*, 56:64-78 (2006), incorporated herein by reference in its entirety). The resulting cell suspension was used to impregnate sterile sponges or Viscopearl in 50 ml Corning plastic tubes to 75%-85% WAC. The tubes were sealed with Parafilm® and incubated static for 2-7 days in the darkness at 23° C.±1° C. After incubation, distilled water was added to sponges and containers were subjected to 2 minutes of Vortex treatment. The $OD_{600}$ of resulting cell suspension was measured and CFU/ml was calculated.

Long-Term Viability

Bacterial cells were grown in sponge square pieces (~50 mg dry weight, 6 pieces per 25 ml tube) as described above. The sponges were left at room temperature in Parafilm®-sealed tubes for several weeks. Single sponge pieces were then removed and placed on the surface of LB plates. Outgrowth was monitored visually. Appearance of outgrowth in 24-48 hours was considered as a positive result.

Dual Plate Fungal Inhibition Assay

*Pseudomonas fluorescens* strain Pf-5 were grown in Viscopearl, as described above. Four ⅓ PDA plates were inoculated in the center by a ~6 mm plug of 4-6-day-old *Sclerotinia sclerotiorum* strain Scl 10-3 (also referred to herein as "Scl 10-3") obtained from Dr. L. Porter (USDA-ARS, Prosser, Wash.). The plates were left at 23° C.±1° C. for 24 hours in the darkness to initiate fungal growth. Then, beads of Viscopearl with 120 hours old bacterial cultures were placed at 1 cm from the edges of plates, two per plate on the opposite sides. The plates were additionally incubated for 4-6 days until fungus front met the edge of the plate. Viscopearl beads impregnated with sterile medium were used as negative control. The fungal growth inhibition capacity of bacterial strains was determined as described previously in Ashwini N. and Srividya, S., "Potentiality of *Bacillus subtilis* as Biocontrol Agent for Management of Anthracnose Disease of Chilli Caused by *Colletotrichum gloeosporioides* OGC1," 3 Biotech 4:127-136 (2014), incorporated herein by reference in its entirety. Between 3 and 4 plates per experiment were employed.

Results

*Pseudomonas fluorescens* strain Pf-5 was grown in shredded sponge and in Viscopearl beads. The results presented in Tables 1 and 2 show that fast and reliable growth of the bacteria was observed independent of the type of open-cell matrix upon provision of appropriate nutrients for the bacteria. After 24 hours of incubation, growth was established at ~70-80% of growth observed at 48 hours data (data not shown). Static cultures in impregnated open-cell matrixes showed higher cell accumulation than liquid static culture (Table 1), or in Viscopearl fully covered by medium (Table 2). This reflects better gas mass transfer in structured media considering the fact that liquid cultures were carried in the same media and started with the same inoculum as those carried in sponge or air-exposed Viscopearl.

TABLE 1

Growth of *P. fluorescens* strain Pf-5 in shredded sponge impregnated by liquid medium. Each 50 mL Corning tube received 500 ± 30 mg of dry sterile shredded sponge crumbs. Sponge was then impregnated by 6.5 ml of the medium inoculated with bacteria to make cell concentration at $10^6$ CFU/ml. All tubes (three to five for each experiment) were sealed with Parafilm ®. Two independent experiments were performed. The experiment labelled "1L" received 6.5 ml of inoculated medium but no sponge as part of experiments #1 to serve as a control. The sealed tubes were incubated for 48 hours.

| Experiment # | $OD_{600}$ AVE | CFU/mL* |
|---|---|---|
| 1 | 5.82 | 9.46 ± 0.21 |
| 2 | 5.86 | 9.47 ± 0.49 |
| 1/L | 1.722 | 8.94 ± 0.024 |

*Data are the means and Standard Deviation

TABLE 2

Growth of *P. fluorescens* strain Pf-5 in Viscopearl impregnated by liquid medium. Each 50 mL Corning tube received 500 ± 7 mg of sterile Viscopearl. Three independent experiments were performed (#1 through #3). There were three tubes per experiment. Viscopearl beads in each tube were impregnated with 2.0 ml of medium inoculated by $10^6$ CFU/ml of bacteria. Experiments labelled "1/D" received 5 ml of inoculated medium to cover all the beads with liquid as part of experiment #1. All tubes were sealed with Parafilm ® and were incubated for 48 hours.

| Experiment # | OD600 AVE | LOG CFU/ml* |
|---|---|---|
| 1 | 4.28 | 9.33 ± 0.11 |
| 2 | 5.22 | 9.42 ± 0.092 |
| 3 | 4.62 | 9.36 ± 0.24 |
| 1/D | 1.634 | 8.91 ± 0.029 |

*Data are the means and Standard Deviation

Long-term survival of bacteria grown in sponge was tested as described above. *Pseudomonas fluorescens* strain Pf-5 was tested after 11 weeks of storage at room temperature (23° C.±3° C.). The culture produced visible colonial growth on the LB plates' surfaces after 24 hours of incubation. As can be concluded from these results, after growth in the open-cell matrix, the microbes can continue to be stored in the matrix for a significant time before deployment.

Next, a dual plate inhibition assay was employed to test the effect of *P. fluorescens* grown in the open-cell matrix on development of the plant pathogenic fungus, *S. sclerotiorum* strain Sd 10-3. Results presented in Table 3 showed that *P. fluorescens* grown in Viscopearl inhibited pathogen growth. About the same level of inhibition was obtained with *P. fluorescens* grown in household sponge pieces (data not shown). These results illustrate the possibility of cultivation in open-cell matrixes and subsequent application of bacteria with pesticidal features to suppress development of plant-pathogenic microorganisms.

TABLE 3

Dual plate inhibition of *S. sclerotiorum* strain Scl 10-3 by *P. fluorescens* strain Pf-5.

| Experiment # | Scl 10 Growth Inhibition by *P. fluorescens* Pf-5, %* |
|---|---|
| 1 | 42.46 ± 6.10 |
| 2 | 48.36 ± 17.18 |

*Data are the means and Standard Deviation

Conclusion

These data provide further confirmation that beneficial microorganisms can be successfully cultured on solid, porous substrates, such as cellulosic sponge and beads. In this illustrative example, an additional Gram negative bacteria, *P. fluorescens*, was successfully cultured on multiple forms of solid, open-celled substrates. The cultures established on the solid substrates were able to maintain viability after long-term storage. Additionally, the cultures were demonstrated to retain anti-fungal properties without requiring any further processing or isolation from the solid growth substrate. Thus, these data further demonstrate the utility and efficacy of generating an anti-fungal formulation that contains the biologic component that remains in association with its solid growth substrate.

Example 2

This example describes an additional study demonstrating the efficacy of another formulation that combines an open-cell solid substrate and the active microbial culture of Gram positive bacteria, *Bacillus amyloliquefaciens*, established thereon to inhibit the growth of a fungal plant pathogen.

Methods and Materials

Solid Substrate Preparation for Growth Experiments

As described above in Example 1.

Solid Substrate Absorption Capacity

As described above in Example 1.

Bacterial Growth in Cellulosic Substrates

*Bacillus amyloliquefaciens* strain FZB42 (also referred to herein as "FZB42") was obtained from The *Bacillus* Genetic Stock Center, Columbus, Ohio, and was maintained on Luria Broth (LB) agar and grown in LB at 23° C.±1° C. (see Idris, E. E. S., et al., "Use of *Bacillus subtilis* as Biocontrol Agent. VI. Phytohormone Like Action of Culture Filtrates Prepared From Plant Growth-Promoting *Bacillus amyloliquefaciens* FZB24, FZB42, FZB45 and *Bacillus subtilis* FZB37," *J. Plant Dis. Prot.,* 111:583-597 (2004), incorporated herein by reference in its entirety) the same way as described for *P. fluorescens* Pf-5. $OD_{600}$ for *B. amyloliquefaciens* strain FZB42 at 0.1 corresponds to $7\times10^8$ CFU/ml (see Talboys, P. J., et al., "Auxin Secretion by *Bacillus amyloliquefaciens* FZB42 Both Stimulates Root Exudation and Limits Phosphorus Uptake in *Triticum aestivum,*" *BMC Plant Biology* 14:51 (2014), incorporated herein by reference in its entirety).

Long-Term Viability

As described above in Example 1.

Dual Plate Fungal Inhibition Assay

*Bacillus amyloliquefaciens* strain FZB42 were grown in Viscopearl, as described above. Four ⅓ PDA plates were inoculated in the center by a ~6 mm plug of 4-6-day-old *Sclerotinia sclerotiorum* strain Scl 10-3 obtained from Dr. L. Porter (USDA-ARS, Prosser, Wash.). The plates were left at 23° C.±1° C. for 24 hours in the darkness to initiate fungal growth. Then, beads of Viscopearl with 120 hours old bacterial cultures were placed at 1 cm from the edges of plates, two per plate on the opposite sides. The plates were additionally incubated for 4-6 days until fungus front met the edge of the plate. Viscopearl beads impregnated with sterile medium were used as negative control. The fungal growth inhibition capacity of bacterial strains was determined as described previously in Ashwini N. and Srividya, S., "Potentiality of *Bacillus subtilis* as Biocontrol Agent for Management of Anthracnose Disease of Chilli Caused by *Colletotrichum gloeosporioides* OGC1," 3 Biotech 4:127-136 (2014), incorporated herein by reference in its entirety. Between 3 and 4 plates per experiment were employed.

Results

*Bacillus amyloliquefaciens* strain FZB42 were grown in shredded sponge and in Viscopearl beads. The results presented in Tables 4 and 5 show that fast and reliable growth of the bacteria was observed independent of the type of open-cell matrix upon provision of appropriate nutrients for the bacteria. FZB42 cultures resulted in a higher CFU relative to *Pseudomonas fluorescens* strain Pf-5 (described above in Example 1), likely because a richer medium (LB) was used to grow the FZB42 bacteria. After 24 hours of incubation, growth was established at ~70-80% of growth observed at 48 hours (data not shown). Static cultures in impregnated open-cell matrixes showed higher cells accumulation than liquid static culture (Table 4), or in Viscopearl fully covered by medium (Table 5). As in Example 1, this data reflects better gas mass transfer in structured media considering the fact that liquid cultures were carried in the same media and started with the same inoculum as those carried in sponge or air-exposed Viscopearl.

TABLE 4

Growth of B. amyloliquefaciens strain FZB42 in shredded sponge impregnated by liquid medium. Each 50 mL Corning tube received 500 ± 30 mg of dry sterile shredded sponge crumbs. Sponge was then impregnated by 6.5 ml of the medium inoculated with bacteria to make cell concentration at $10^6$ CFU/ml. All tubes (three to five for each experiment) were sealed with Parafilm ®. Two independent experiments were performed. The experiment labelled "1L" received inoculated medium but no sponge as part of experiments #1 to serve as a control. The sealed tubes were incubated for 48 hours.

| Experiment # | $OD_{600}$ AVE | CFU/mL* |
|---|---|---|
| 1 | 10.5 | 10.87 ± 0.81 |
| 2 | 9.30 | 10.81 ± 0.73 |
| 1/L | 2.32 | 10.21 ± 0.037 |

*Data are the means and Standard Deviation

TABLE 5

Growth of B. amyloliquefaciens strain FZB42 in Viscopearl impregnated by liquid medium. Each 50 mL Corning tube received 500 ± 7 mg of sterile Viscopearl. Three independent experiments were performed (#1 through #3). There were three tubes per experiment. Viscopearl beads in each tube were impregnated with 2.0 ml of medium inoculated by $10^6$ CFU/ml of bacteria. Experiments labelled "1/D" received 5 ml of inoculated medium to cover all the beads with liquid as part of experiment #1. All tubes were sealed with Parafilm ® and were incubated for 48 hours.

| Experiment # | $OD_{600}$ AVE | LOG CFU/ml |
|---|---|---|
| 1 | 9.49 | 10.82 ± 0.49 |
| 2 | 10.91 | 10.88 ± 0.31 |
| 3 | 10.32 | 10.86 ± 0.83 |
| 1/D | 1.93 | 10.13 ± 0.094 |

*Data are the means and Standard Deviation

Long-term survival of bacteria grown in sponge was tested as described above. B. amyloliquefaciens strain FZB42 was tested after 3 weeks of storage at room temperature (23° C.±3° C.). The culture produced visible colonial growth on the LB plates surfaces after 24 hours incubation. As can be concluded from these results, after growth in the open-cell matrix, the microbes can continue to be stored in the matrix for a significant time before deployment.

Next, a dual plate inhibition assay was employed to test the effect of B. amyloliquefaciens grown in the open-cell matrix on development of the plant pathogenic fungus, S. sclerotiorum strain Scl 10-3. Results presented in Table 6 showed that B. amyloliquefaciens grown in Viscopearl inhibited pathogen growth. These results illustrate the possibility of cultivation in open-cell matrixes and subsequent application of bacteria with pesticidal features to suppress development of plant-pathogenic microorganisms.

TABLE 6

Dual plate inhibition of S. sclerotiorum strain Scl 10-3 by B. amyloliquefaciens strain FZB42.

| Experiment # | Scl 10 Growth Inhibition by B. amyloliquefaciens, %* |
|---|---|
| 1 | 52.08 ± 8.57 |
| 2 | 50.40 ± 7.88 |

*Data are the means and Standard Deviation

Conclusion

These data provide further confirmation that beneficial microorganisms, such as the Gram positive bacteria B. amyloliquefaciens, can be successfully cultured on solid, porous substrates, such as cellulosic sponge and beads. The cultures established on the solid substrates were able to maintain viability after long-term storage. Additionally, the cultures were demonstrated to have anti-fungal properties without requiring any further processing or isolation from the solid growth substrate. Thus, these data further demonstrate the utility and efficacy of generating an anti-fungal formulation that contains the biologic component that remains in association with its solid growth substrate.

Example 3

This example describes an additional study demonstrating the efficacy of a formulation that combines an open-cell solid substrate and the active fungal culture of Trichoderma sp. established thereon to inhibit the growth of a fungal plant pathogen.

Methods and Materials
Solid Substrate Preparation for Growth Experiments
As described above in Example 1.
Solid Substrate Absorption Capacity
As described above in Example 1.
Fungal Growth in Cellulosic Substrates Trichoderma sp. ATCC 74015 (also referred to herein as "ATCC 74015") was maintained on Potato Dextrose Agar (PDA; ATCC Medium 336) plates. 1 g Viscopearl in 25 ml glass tubes was impregnated with 5 ml of sterile liquid Potato Dextrose Broth (PDB) inoculated with a scoop of fungal spores/mycelium from a 4-5 day plate. Tubes were sealed in Parafilm® and incubated at room temperature in dim light for 10 to 30 days before use. Culture viability was tested by placing a bead of Viscopearl on the surface of PDA. Outgrowth of mycelia in 24-48 hours was considered as positive viability.

Comparing Fungus Grown from Viscopearl and from PDA Plates

Ten (10) days after inoculating the Viscopearl with Trichoderma sp ATCC 74015, as described above, four beads were removed and a single bead placed in the center of each of four PDA plates. At the same time 5 mm plugs of actively growing ATCC 74015 was taken from the leading growing edge of a 3-day-old PDA plate and placed in the center of each of four PDA plates. The plates were examined every 24 hours and the diameter of the colony measured. After 96 hours, when the mycelia reached the edge of the plate, there was neither a statistical nor a visual difference between any of the plates.

The same experiment was performed thirty (30) days after inoculating the Viscopearl. Again, there was no difference in colony growth.

The growth of the fungus from the Viscopearl was as active as the fungus from the leading edge of 3-day-old actively growing mycelia on PDA.

Dual Plate Fungal Inhibition Assay Comparing Fungus Grown on Viscopearl and on PDA Plates Dual plate inhibition assay with Trichoderma sp. ATCC 74015 and Sclerotinia sclerotiorum Scl 10-3 was performed according to known techniques. See, e.g., Matroudi S., et al., "Antagonistic Effects of Three Species of Trichoderma sp. on S. sclerotiorum, The Causal Agent of Canola Stem Rot," Egyptian Journal of Biology, 11:37-44 (2009), incorporated herein by reference in its entirety. Briefly, Trichoderma sp. ATCC 74015 was grown in Viscopearl, as described above.

For dual cultures, either a mycelial plug of actively growing Trichoderma sp. ATCC 74015 isolate (5 mm diameter) incubated on potato dextrose agar or a Viscopearl bead inoculated with ATCC 74015 was placed about 1 cm from the edge of each PDA petri dish. A mycelial plug of *S. sclerotiorum* strain Scl 10-3 removed from the colony margin of a 3-day-old culture grown on potato dextrose agar was placed 6 cm away from the inoculation site of ATCC 74015 in the same petri dish. Petri dishes similarly inoculated with ATCC 74015 or Scl 10-3 cultures alone were used as controls. Plates were incubated at 22° C., and were examined daily for the formation of inhibition zones between fungal cultures. Radial growth reduction was calculated in relation to growth of the control as follows:

% Inhibition of radial mycelial growth=$[(C-T)/C]\times 100$ where C is the radial growth measurement of the pathogen in control plates, and T is the radial growth of the pathogen in presence of ATCC 74015 (Matroudi, et al., 2009).

Results

*Trichoderma* sp. ATCC 74015 was grown in Viscopearl/PDB as described above. At 10 and 30 days, single beads were removed and placed on PDA surface. Visible mycelial outgrowth from the beads was clearly seen in 48 hours later. Fungal mycelium was also clearly visible in the Viscopearl mass (not shown).

Dual plate inhibition assays were performed to assess competition between fungal species. Using the method described above, the percent inhibition of *S. sclerotiorum* strain Scl 10-3 by *Trichoderma* sp. ATCC 74015 using either the 10 and 30-day-old beads or a plug of actively growing mycelia was the same at 55±4%.

Conclusion

These data demonstrate that fungi, such as *Trichoderma* sp., can be successfully cultured on the disclosed solid, porous substrates, such as cellulosic sponge and beads. Furthermore, the fungal culture in association with its solid substrate served as a formulation that successfully competed with a pathogenic fungus. The formulation possessed antifungal properties without requiring any further processing or isolation of the fungal culture from the solid growth substrate. Thus, these data further demonstrate the utility and efficacy of generating an anti-fungal formulation that can contain a wide variety of biologic components, which remain in association with its solid growth substrate as it is applied to the plant environment.

While illustrative embodiments have been described, it will be appreciated that various changes can be made therein without departing from the spirit and scope of the invention.

The embodiments of the invention in which an exclusive property or privilege is claimed are defined as follows:

1. A biologically active formulation configured to be applied directly to a seed or plant environment, comprising a solid substrate comprised of a plurality of porous particles and one or more populations of metabolically active microorganisms, wherein:

each particle of the plurality of porous particles is no larger in size than 5 mm;

each particle of the plurality of porous particles is comprised of a plurality of interconnected open cells and/or channels that form an open cell matrix;

the porous particles contain a liquid medium, provided that the open cell matrix is impregnated with the liquid medium, the porous particles are not covered by the liquid medium, the liquid medium is at a volume of about 75% to about 85% of the water absorption capacity (WAC) of the porous particle, and a plurality of the porous particles are in direct gaseous communication with the outside environment; and the one or more populations of metabolically active microorganisms are in contact with the liquid medium and present in the open cell matrix of the individual particles.

2. The formulation of claim 1, wherein the one or more populations of metabolically active microorganisms can produce one or more biologically active compounds that affect a plant and its environment.

3. The formulation of claim 1, wherein the one or more populations of microorganisms comprise a prokaryote selected from archaebacteria, Gram negative eubacteria, Gram positive eubacteria, cyanobacteria, or any combination thereof.

4. The formulation of claim 1, wherein the one or more populations of microorganisms comprises a eukaryote selected from fungi, protozoa, or both.

5. The formulation of claim 1, wherein the one or more populations of microorganisms, or a portion of the one or more populations of microorganisms, form a biofilm within the open cell matrix.

6. The formulation of claim 1, wherein the formulation does not include a biofilm.

7. The formulation of claim 1, wherein the plurality of interconnected open cells each have a diameter ranging from about 10 μm to about 1,000 μm.

8. A method for conditioning a plant growth environment, comprising applying the biologically active formulation of claim 1 to a plant or a plant growth environment.

9. The method of claim 8, wherein the plant growth environment is soil, soil mixes, hydroponic medium, or any surface of the plant.

10. The method of claim 8, wherein the applying of the biologically active formulation is to a seed, vegetative cutting, root, rhizome, bulb, tuber, stem, flower, fruit, and/or leaf of the plant.

11. The method of claim 8, wherein the one or more populations of microorganisms comprise a microorganism capable of negatively affecting a targeted pest or weed.

12. The method of claim 8, wherein the one or more populations of microorganisms comprise a microorganism that can consume a pollutant that is toxic or inhibitory to the plant.

13. The formulation of claim 2, wherein the one or more biologically active compounds comprise an agent selected from the group consisting of a pesticide, a nutrient, a biostimulant, a chelator, an enzyme, and an antibiotic.

14. The formulation of claim 3, wherein the Gram negative eubacteria is selected from *Pseudomonas, Lysobacter, Rhizobium, Serratia, Methylobacterium, Agrobacterium, Azospirillum, Azotobacter*, or any combination thereof.

15. The formulation of claim 3, wherein the Gram positive eubacteria is selected from *Bacillus, Paenibacillus, Streptomyces, Arthrobacter*, or any combination thereof.

16. The method of claim 8, wherein the one or more populations of microorganisms compete for resources naturally utilized by other organisms present on the plant or in the plant environment.

17. The method of claim 8, wherein the one or more populations of microorganisms comprise a microorganism that is a predator microorganism of an undesired microorganism.

18. The method of claim 8, wherein the predator microorganism is a predaceous fungi.

19. The formulation of claim 1, wherein the formulation is present in a container selected from a plastic, metal, or glass container.

20. The formulation of claim 14, wherein the Gram negative eubacteria comprises *Pseudomonas fluorescens* Pf-5.

\* \* \* \* \*